US00RE38115E

(19) United States
(12) Reissued Patent
Smith et al.

(10) Patent Number: US RE38,115 E
(45) Date of Reissued Patent: May 6, 2003

(54) DEXTROMETHORPHAN AND AN OXIDASE INHIBITOR FOR TREATING INTRACTABLE CONDITIONS

(75) Inventors: Richard Alan Smith, La Jolla, CA (US); Jonathan M. Licht, San Diego, CA (US)

(73) Assignee: Center for Neurologic Study, La Jolla, CA (US)

(21) Appl. No.: 10/052,698

(22) PCT Filed: Sep. 22, 1994

(86) PCT No.: PCT/US94/10771

§ 371 (c)(1), (2), (4) Date: Sep. 19, 1996

(87) PCT Pub. No.: WO96/09044

PCT Pub. Date: Mar. 28, 1996

Related U.S. Patent Documents

Reissue of:
(64) Patent No.: 5,863,927
Issued: Jan. 26, 1999
Appl. No.: 08/464,792
Filed: Sep. 19, 1996

(51) Int. Cl.[7] ..... A61K 31/44; A61K 31/265; A61K 31/135

(52) U.S. Cl. ..... 514/289; 514/305; 514/491; 514/649; 514/651; 514/652; 514/654

(58) Field of Search ..... 514/289, 305, 514/491, 649, 651, 652, 654

(56) References Cited

U.S. PATENT DOCUMENTS

| | | | | | |
|---|---|---|---|---|---|
| 4,316,888 | A | * | 2/1982 | Nelson | 424/127 |
| 5,166,207 | A | * | 11/1992 | Smith | 514/270 |
| 5,206,248 | A | * | 4/1993 | Smith | 514/289 |
| 5,350,756 | A | * | 9/1994 | Smith | 514/289 |
| 5,352,683 | A | * | 10/1994 | Mayer et al. | 514/289 |
| 5,366,980 | A | * | 11/1994 | Smith | 514/289 |
| 5,502,058 | A | * | 3/1996 | Mayer et al. | 514/289 |

OTHER PUBLICATIONS

Dickenson, A.H., "A cure for wind up: NMDA receptor antagonist as potential analgesics," *Trends in Pharm. Sci., 11*:307–309 (1990).*

Dickenson, A.H., et al., "Dextromethorphan and levorphanol on dorsal horn nociceptive neurones in the rat," *Neuropharmacology, 30*: 1303–1308 (1991).*

France, C. P., et al., "Analgesic Effects of Phencyclidine–Like Drugs in Rhesus Monkeys," *J. Pharmacol. Exp. Therapeutics, 250*: 197–201 (1989).*

Mao, J., et al., "Intrathecal treatment with dextrorphan or ketamine potently reduces pain–related behaviors in a rat model of peripheral mononeuropathy," *Brain Research, 605*: 164–168 (1993).*

McCarthy, J.P., "Some less familiar drugs of above," *Med. J. Australia 1971 (2)*: 1078–1081 (1971).*

McQuay, H. J., et al., "Dextromethorphan for the treatment of neurophatic pain: a double–blind randomised controlled crossover trial with integral n–of–1 deisgn," *Pain, 59*: 127–133 (1994).*

Tortella, F.C., et al., "Dextromethorphan and neuromodulation: old drug coughs up new activities," *Trends in Pharm. Sci, 10*: 501–507 (1989).*

Zhang et al. "Dextromethorphan: Enhancing its Systemic Availablity by Way of Low–dose QWuinidine–mediated Inhibition of Cytochrome P45O2D6," *Clin. Pharm. ? Ther.*, 51(6) :647–655 (1992).*

* cited by examiner

*Primary Examiner*—Phyllis G. Spivack
(74) *Attorney, Agent, or Firm*—Knobbe, Martens, Olson & Bear, LLP

(57) ABSTRACT

Methods are disclosed for increasing the effectiveness of dextromethorphan in treating chronic or intractable pain, for treating tinnitus and for treating sexual dysfunction comprising administering dextromethorphan in combination with a therapeutically effective dosage of a debrisoquin hydroxylase inhibitor. A preferred combination is dextromethorphan and the oxidative inhibitor quinidine.

22 Claims, 1 Drawing Sheet

DEXTROMETHORPHAN AND AN OXIDASE INHIBITOR FOR TREATING INTRACTABLE CONDITIONS

Matter enclosed in heavy brackets [ ] appears in the original patent but forms no part of this reissue specification; matter printed in italics indicates the additions made by reissue.

[This application is a 371 of PCT/US94/10771, filed Sep. 22, 1994.] *This application is the 35 U.S.C. §371 national stage application of PCT application No. PCT/US94/10771 filed Sep. 22, 1994, which is a continuation-in-part of application Ser. No. 08/114,845 filed Sep. 2, 1993, issued as U.S. Pat. No. 5,366,980 on Nov. 22, 1994, which is a continuation-in-part of application Ser. No. 07/896,053 filed Jun. 9, 1992, now abandoned.*

BACKGROUND OF THE INVENTION

This invention relates to pharmacology. More specifically, the invention relates to compositions of matter useful for preparing medicaments for the treatment of various disorders.

A number of chronic disorders have symptoms which are known to be very difficult to treat, and often fail to respond to safe, non-addictive, and non-steroid medications. Such disorders, such as intractable coughing, fail to respond to conventional medicines and must be treated by such drugs as codeine, morphine, or the anti-inflammatory steroid prednisone. These drugs are unacceptable for long-term treatment due to dangerous side-effects, long-term risks to the patient's health, or the danger of addiction. Other disorders, such as dermatitis, have no satisfactory treatment for the severe itching and rash at this time. Drugs such as prednisone and even tricyclic antidepressants, as well as topical applications, have been tried, but do not appear to offer substantial and consistent relief.

Chronic pain due to conditions such as stroke, cancer, trauma, as well as neuropathic pain resulting from conditions such as diabetes and shingles (herpes zoster), for example, is also a problem which resists treatment. Chronic pain is estimated to affect millions of people. A variety of therapies for this type of pain have been tried, but there remains a need for safe and effective treatments.

The compound dextromethorphan, or (+)-3-methoxy-N-methylmorphinan, has been used as a cough suppressant ingredient in cough syrups. Dextromethorphan has also been tested as a potential therapeutic agent for stroke, and progressive neurodegenerative diseases such as Parkinson's disease, Alzheimer's disease and amyotrophic lateral sclerosis. However, the effectiveness of dextromethorphan for the treatment of any disorder has been limited because it is rapidly broken down by the liver and excreted in most individuals.

It is an object of the present invention to provide a combination of compounds useful for the preparation of medicaments which will effectively treat formerly intractable conditions not responsive to other medications. It is also an object of the present invention to provide medicaments which are safe, non-addictive, and relatively free of side-effects for patients suffering from long-term intractable conditions.

SUMMARY OF THE INVENTION

The present invention provides compounds which are useful in the preparation of medicaments for the treatment of a variety of disorders including intractable coughing, dermatitis, chronic pain, tinnitus and sexual dysfunction. These compounds are a therapeutically effective dosage of dextromethorphan and a therapeutically effective dosage of a second agent, an inhibitor of enzymatic dextromethorphan oxidation. This combination of compounds can be administered together, or individually. A preferred combination is dextromethorphan and the oxidative inhibitor quinidine. Inhibitors which may also be used include quinine, yohimbine, fluoxetine, haloperidol, ajmaline, lobeline, and pipamperone.

DETAILED DESCRIPTION OF THE PREFERRED EMBODIMENTS

Definitions

Figure 1:
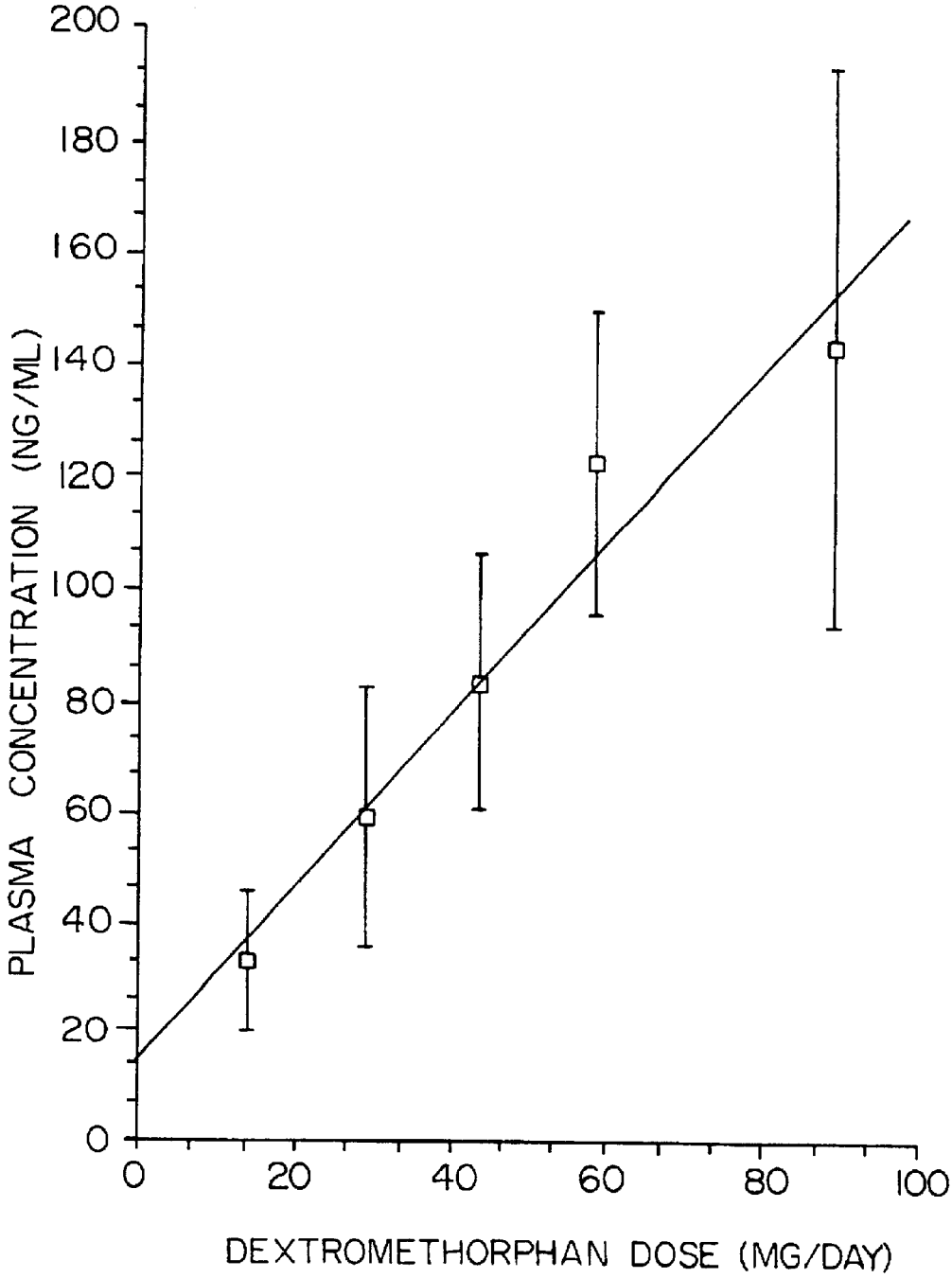
FIG. 1 shows the relationship between DM oral dosages and DM plasma concentrations in patients receiving 150 mg/day of quinidine orally.

As used herein the term dextromethorphan (hereinafter, DM) refers to (+)-3-methoxy-N-methylmorphinan, or therapeutically effective salts and analogs thereof.

As used herein the term "antioxidants" or "oxidative inhibitors" refers to inhibitors capable of inhibiting the oxidation of DM by the liver enzyme debrisoquin hydroxylase.

As used herein, the term "intractable" or "refractory" coughing refers to coughing that will not respond adequately to non-addictive, non-steroid medications.

As used herein, the term "dermatitis" or "eczema" refers to a skin condition which includes visible skin lesions which may be accompanied by an itching or burning sensation on the skin. This condition does not readily respond to non-prescription drugs, lotions, or ointments.

As used herein the term "chronic pain" refers to long-term pain resulting from conditions such as stroke, cancer and trauma, as well as neuropathic pain due to deterioration of nerve tissue such as postherpetic neuralgia (PHN) resulting from herpes zoster infection, and diabetic neuropathy resulting from long-time diabetes.

As used herein the term "tinnitus" refers to a syndrome characterized by a high-pitched ringing in the ears thought to be induced by loss of motility of the outer hair cells of the cochlea of the ear.

The present invention provides compositions for use in the preparation of medicaments for the effective treatment of a variety of chronic and intractable disorders which failed to respond to other treatments. These compositions are a therapeutically effective dosage of dextromethorphan (DM), or a pharmaceutically acceptable salt or analog thereof, in combination with a therapeutically effective dosage of an inhibitor of enzymatic dextromethorphan oxidation by the liver enzyme debrisoquin hydroxylase. The chronic and intractable disorders which have responded to medicaments containing a dextromethorphan/antioxidant combination include intractable coughing, dermatitis, chronic pain and tinnitus. Relatively potent antioxidants include quinidine and quinine. Other antioxidants which are milder include yohimbine, fluoxetine, haloperidol, ajmaline, lobeline, pipamperone.

It has been found that the use of quinidine and other oxidation inhibitors when administered in conjunction with DM has pronounced effect in increasing and stabilizing the quantity of DM circulating in the blood of a patient. This effect is discussed in U.S. Pat. No. 5,166,207 to Smith, issued Nov. 24, 1992, and in Zhang, Y., Clin. Pharmacol. Ther. 51: 647–655 (1992), both of which are herein incorporated by reference.

Dextromethorphan (hereinafter DM) is the common name for (+)-3-methoxy-N-methylmorphinan. This compound is described in detail in Rodd et al., Chemistry of Carbon Compounds, Elsevier Publ., New York (1960), for example, which is herein incorporated by reference. DM is a non-addictive opioid having a dextrorotatory enantiomer (mirror image) of the morphinan ring structure which forms the molecular core of most opiates.

DM has been used as an ingredient of cough suppressant in over-the-counter cough syrup. The cough-suppressing activity of DM is thought to be due primarily to its actions as an agonist on a class of neuronal receptors known as sigma receptors or high-affinity dextromethorphan receptors. Although these receptors are sometimes referred to as sigma opiate receptors, it is not clear whether they are in fact opiate receptors. Sigma receptors are inhibitory receptors and the activation of these receptors by DM or other sigma agonists causes the suppression of certain types of nerve signals. Dextroinethorphan is also thought to act on another class of receptors known as N-methyl-D-aspartate (NDMA) receptors, which are one type of excitatory amino acid (EAA) receptor. Unlike its agonist activity at sigma receptors, DM acts as an antagonist at NMDA receptors, suppressing the transmission of nerve impulses mediated through NMDA receptors. Since NMDA receptors are excitatory receptors, the action of DM as an NMDA antagonist also results in the suppression of nerve signals. In addition, DM has been reported to suppress activity at neuronal calcium channels. It is the antagonist activity of DM at NMDA receptors which is through to be one of the common links between some of the various conditions which respond to medicaments containing a DM/antioxidant combination.

When used in therapeutic applications, DM disappears rapidly from the bloodstream of most individuals, as described in Dayer et al., Clin. Pharmacol. Ther. 56:34–30 (1989), Vetticaden et al., Pharmaceut. Res. 6:13–19 (1989), and Ramachander et al., J. Pharm. Sci. 66: 1047–1049 (1977), which are herein incorporated by reference. DM is broken down in the liver into several metabolites. DM can be oxidized by O-dimethylation, in which one of the methyl groups is removed and two metabolites, dextrorphan and 3-methoxymorphinan, are produced. If the second methyl group is removed, the resulting metabolite is 5-hydroxymorphinan. Dextrorphan is known to have many of the biological activities of DM. However, dextrorphan and 5-hydroxymorphinan become covalently bonded to other compounds in the liver, primarily glutathione to form glucuronide or sulfate conjugates, which can not readily cross the blood-brain barrier and which are quickly eliminated from the body in the urine.

The particular enzyme primarily responsible for DM oxidation is debrisoquin hydroxylase, also known as sparteine monooxygenase, and also referred to in the literature variously as cytochrome P-450$_{DB}$, as cytochrome P-450db1 (or db1 ), and as cytochrome P-4502D6. Hereinafter, this enzyme is referred to as debrisoquin hydroxylase. Debrisoquin hydroxylase belongs to the family "cytochrome P-450" enzymes, or as "cytochrome oxidase" enzymes. These enzymes typically found in high concentrations in liver cells primarily in liver microsomes, and in lower concentrations in various other organs and tissues such as the lungs. By oxidizing lipophilic compounds, cytochrome oxidase enzymes eliminate compounds from the body that might otherwise act as toxins or accumulate to undesired levels. Typically, oxidation renders lipophilic compounds more soluble in water and therefore, more easily eliminated in the urine or in aerosols exhaled out of the lungs. The debrisoquin hydroxylase enzyme apparently is also present in brain tissue (Fonne-Pfister et al., Biochem. Biophys. Res. Communic. 148: 1144–1150 (1987), Niznik et al., Arch. Biochem. Biophys. 26:424–432 (1990), Tyndate et al., Mol. Pharmacol. 40:63–68 (1991)), although its function in the brain is not fully understood.

Dextromethorphan is widely available over-the-counter in cough syrups, at dosages up to about 120 mg/day for an adult. This invention anticipates DM dosages in the range of about 20 mg/day to about 200 mg/day, preferably in the range of 20 to 150 mg/day, depending on factors such as the weight of the patient, the severity of the disorder, and the potency and dosage of the antioxidant agent used in conjunction with DM.

Quinidine is a dextrorotatory steroisomer of quinine. Quinidine is commonly used to treat cardiac arrhythmias, and is considered a relatively strong cardiac medicine. Quinidine is commercially available from a number of sources, for example, A H. Robins, Richmond, Va., but is available to the public only with a doctor's prescription. Both DM and quinidine are commercially available in powder form, and capsules of a specific dosage can be prepared as desired by commercial vendors. The dosage of quinidine which was found to provide a major increase in DM concentration in the blood of most patients was equal to or less than 150 mg/day, depending on the individual. The present invention contemplates dosages ranging from 50 mg/day to 300 mg/day, preferably from 50 mg/day to 150 mg/day. In some patients a dosage of about 50 mg/day is found to be effective. In contrast the dosage used for anti-arrhythmic control in cardiac patients is between 600–1200 mg/day.

A number of antioxidants other than quinidine have already been identified in the literature, using in vitro screening. These are reported in Inaba et al., Drug Metabolism and Disposition 13:443–447 (1985), Fonne-Pfister et al., Biochem. Pharmacol. 37:3829–3835 (1988) and Broly et al., Biochem. Pharmacol. 39:1045–1053 (1990), all of which are herein incorporated by reference. As reported in Inaba et al., agents with a $K_i$ value (Michaelis-Menton inhibition values) of 50 micromolar or lower include nortriptyline, chlorpromazine, domperidone, haloperidol, pipamperone, labetalol, metaprolol, oxprenolol, propranolol, timolol, mexiletine, quinine, diphenhydramine, ajmaline, lobeline, papaverine, and yohimbine. Preferred compounds having particularly potent inhibitory activities include yohimbine, haloperidol, ajmaline, lobeline, and pipamperone, which have $K_i$ values ranged from 4 to 0.33 $\mu$M. In comparison, the $K_i$ value of quinidine is 0.06 $\mu$M. of these inhibitors quinine sulfate, disulfiram, cimetidine, fluoxetine, propranolol, and nortriptyline were tested for the ability to stabilize the concentration of DM in the blood stream, as described in detail in Example 4 below. As expected, the results of these studies show an increase in levels of DM which is not as pronounced as that when DM is co-administered with quinidine. In addition, the results indicated substantial variations between individuals in the effect of each antioxidant. Quinine, having a structure similar to quinidine, was shown to be effective in increasing DM/DRP ratios in the individuals tested. Other drugs showed more variability among individuals. This variability indicates that individual antioxidants would be pre-tested using the methodology described in Example 4 below, before using on patients. It should also be noted that a number of antioxidants have their own pharmaceutical effects, which vary widely, and which would be taken into consideration by a prescribing physician. Dosages of other antioxidants will vary with the antioxidant, and should be determined on an individual basis using the protocal described in Example 4.

In addition to the antioxidants reported above, it has also been found that fluoxetine, sold by Eli Lilly and Co. under the trade name Prozac, is effective in increasing DM concentrations in the blood of some people. For example, a single patient who was taking 20 mg fluoxetine twice a day registered a blood level of 40 ng/ml of DM when administered DM according to the testing outlined in Example 4.

The optimal dosage of both dextromethorphan and any of the antioxidant to be administered to specific patient can be determined by administering various dosages of each drug and then (1) analyzing blood samples to determine the concentration of DM in the circulating blood, and/or (2) evaluating the patient's progress to determine which combination of dosages provides the best result in effectively suppress the symptoms being targeted.

A number of factors influence the dosage of DM and antioxidant which would be appropriate for a particular individual. One very important factor is the individual's ability to metabolize DM. It is known that a substantial fraction of the general public, estimated from 7 to 10%, do not have a properly functioning gene encoding the debrisoquin hydroxylase enzyme. These persons are referred to by doctors and pharmacologists as "poor metabolizers", while those having the gene encoding debrisoquin hydroxylase are known as "extensive metabolizers". "Poor metabolizers" are regarded as somewhat high-risk patients who must be treated with special care and attention, since they are overly sensitive to certain drugs that can be prescribed safely to people who have the full set of cytochrome P450 enzymes.

In addition to the inhibition of debrisoquin hydroxylase, other cytochrome P450 isozymes are also likely to be suppressed by quinidine or other inhibitors, with varying levels of binding affinity. This is described in articles such as Kupfer et al., Lancet ii:517–518 (1984) and Guttendorf et al., Ther. Drug. Monit. 10:490–498 (1988), which are herein incorporated by reference. In addition, cytochrome P-450 enzymes are non-specific to the extent that a single isozyme can react with numerous substrates having widely different chemical structures, and various isozymes are known to have overlapping activity on a single substrate. Accordingly, even though quinidine exerts its most marked effect on debrisoquin hydroxylase, it may suppress a number of other cytochrome P450 enzymes as well, thereby subjecting a patient to a more general loss of normal and desirable liver activity.

Since DM is considered to be a safe drug which is readily available as an over-the-counter medication, it can be used as a convenient tool or probe drug for determining whether a patient is a extensive metabolizer or a poor metabolizer. Such diagnostic tests are performed so that a patient who is a "poor metabolizer" can be identified and protected against various drugs which he or she cannot metabolize properly. However, if a patient is taking a drug such as quinidine, the level of enzymes will be inhibited, and the diagnostic test for identifying "poor metabolizers" will not be accurate, and will reflect the presence of the inhibitor.

In addition, DM may cause side effects in some people such as diarrhea, drowsiness, lightheadedness, or loss of appetite, and in some cases, impotence in male patients. The likelihood and severity of such side-effects will be increased by antioxidants, in direct proportion to the potency of the antioxidant used. Therefore, the DM-quinidine combination or DM-antioxidant combinations disclosed herein is currently anticipated for use only under the supervision of a physician, who would determine the appropriateness of the treatment. All the appropriate precautions should be taken with the use of any antioxidant, as would be appreciated by a physician and others of skill in the art. However, the dosage of quinidine that provides a substantial increase in DM concentration in the blood is only a fraction of the dosages normally used for anti-arrhythmic action.

For some patients, combinations of DM and antioxidants other than quinidine are preferred for preparing medicaments. In some instances, individual may not tolerate quinidine or quinidine-DM combinations, for example, when a patient may be allergic to quinidine, or if a patient is suffering from a heart condition known as a prolonged QT interval, and therefore cannot tolerate quinidine. Less potent oxidation inhibitors are also preferred in combination with DM for example, as a second agent that can be alternated with quinidine to avoid developing a tolerance that would require increasing dosages of quinidine; or for patients who have a moderate condition such as coughing that will not respond adequately to other treatments, but which is not severe enough to require a potent enzyme inhibitor.

It was unexpectedly discovered that DM in conjunction with quinidine was highly effective in reducing the symptoms of "emotional lability". Emotional lability is a complex problem in which patients suffering from bilateral neurological damage typically due to a stroke or head injury or a neurologic disease such as ALS or Alzheimer's disease are unable to control spasmodic emotional outbursts such as explosive laughing or uncontrollable weeping. In patients suffering from brain damage leading to emotional lability, such outbursts often occur at very inappropriate times and without provocation. The ability of DM in conjunction with quinidine to control emotional lability is described in U.S. Pat. No. 5,206,248, issued on Apr. 27, 1993, which is herein incorporated by reference. This effect of DM-quinidine in controlling emotional lability was not observed in any patients who received DM alone.

It has now been found that the combination of compounds described above are extremely effective in medicaments for the treatment for other chronic disorders which do not respond well to other treatments. A DM/antioxidant combination can be used to effectively treat severe or intractable coughing, which has not responded adequately to non-addictive, non-steroid medications. Intractable coughing is a consequence of respiratory infections, asthma, emphysema, and other conditions affecting the pulmonary system.

Tests using a DM-quinidine combination to treat intractable coughing in human patients is described in Example 5 below. In all patients tested, treatment with a combination of DM and an antioxidant provided highly beneficial results with minimal side-effects. These results clearly confirmed the effectiveness and utility of the use of DM-antioxidant in preparing medicaments for treatment of intractable coughing.

This invention also discloses the use of DM in combination with an antioxidant in preparing medicaments for treating dermatitis. As used herein, "dermatitis" or "eczema" is a skin condition characterized by visible skin lesions and/or an itching or burning sensation on the skin. The effectiveness of the DM-quinidine combination for treating dermatitis was first observed as an unexpected beneficial side effect during testing on an ALS patient who happened to suffer from severe dermatitis. This drug combination showed a beneficial effect on dermatitis when subsequently tested by a dermatologic specialist on a non-ALS patient suffering from severe dermatitis. After these initial results, an additional study was conducted on several patients suffering from dermatitis, by administering DM-quinidine capsules orally. The results showed marked relief from the rash and itching. Topical administration of DM or DM-antioxidant containing medicaments is contemplated for person suffering from dermatitis. These results are described in more detail in Example 6.

It is also contemplated that DM alone can be effective in treating dermatitis for certain patients who are classified as "poor metabolizers" due to a genetic inability to express functional copies of the debrisoquin hydroxylase enzyme. For these individuals DM alone, at safe dosages, will be sufficient to treat the dermatitis effectively without requiring concomitant use of an antioxidant to increase DM levels in the blood.

The present invention also provides for the use of DM and an antioxidant in medicaments for the treatment of chronic pains from conditions such as stroke, trauma, cancer, and pain due to neuropathies such as herpes zoster infections, and diabetes.

Neuropathic pain includes postherpetic neuralgia, and diabetic neuropathy. Postherpetic neuralgia (PHN) is a complication of shingles and occurs in approximately 10 percent of patients with herpes zoster. The incidence of PHN increases with age. Diabetic neuropathy is a common complication of diabetes which increases with the duration of the disease. The pain for these types of neuropathies can be described as the following: burning steady pain often punctuated with stabbing pains, pins and needles pain, or toothache-like pain. The skin can be sensitive with dysesthetic sensations to even light tough and clothing. The pain can be exacerbated by activity, temperature change or emotional upset. The pain can be so severe as to preclude daily activities or result in sleep disturbance or anorexia. The mechanisms involving in producing pain of these types are not well understood, but may involve degeneration of myelinated nerve fibers. It is known that in diabetic neuropathy both small and large nerve fibers deteriorate and therefore the thresholds for tolerance of thermal sensitivity, pain, and vibration are reduced over time. Dysfunction of both large and small fiber functions is more severe in the lower limbs when pain develops. Most of the physiological measurement of nerves that can be routinely done in patients experiencing neuropathic pain demonstrate a slowing of nerve conduction over time. To date, treatment for neuropathic pain has been less than universally successful.

Human patients suffering from chronic pain due to stroke, diabetes, and other causes, were placed on a dosage of DM-quinidine taken orally. All patients experienced some degree of pain relief after receiving DM-quinidine for two to four weeks. This study is described in Example 7 below.

It was noted that a side-effect suffered by some of the male patients in earlier emotionality studies and the dermatitis studies described in Example 7 included instances of impotence. This impotence persisted until the patient stopped taking medication containing DM-quinidine. Therefore, DM-antioxidants containing medicaments are contemplated for the treatment of sexual dysfunctions including priapism or premature ejaculation.

One of the patients involved in the pain studies also suffered from tinnitus, a syndrome characterized by a high pitched ringing in the ears. After treatment with DM/quinidine, the patient reported that the ringing had ceased. Therefore, based on this evidence and the involvement of NMDA receptors in the cochlear system, the use of DM/antioxidants in the preparation of medicaments for the treatment of tinnitus is also contemplated by the present invention.

The medicaments used for treating the various disorders described above are prepared from DM and an appropriate antioxidant, or alternatively from the salts and analogs of DM and the various antioxidants. The terms "salt" and "analog" are used in their conventional pharmaceutical sense, and are limited to pharmacologically acceptable and therapeutically effective salts and analogs of dextromethorphan or an antioxidant as discussed herein. The term "pharmacologically acceptable" embraces those characteristics which make a salt or analog suitable and practical for administration to humans; for example, such compounds must be sufficiently chemically stable under reasonable storage conditions to have an adequate shelf life, they must be physiologically acceptable when orally ingested, and they must not be addictive or cause unacceptable side effects. Acceptable salts can include alkali metal salts as well as salts of free acids or free bases. Acids that may be employed to form acid addition salts include inorganic acids such as sulfate or chloride salts, as well as organic acids. Alkali metal salts or alkaline earth metal salts might include, for example, sodium, potassium, calcium or magnesium salts. All of these salts can be prepared by conventional means. Various salts of the compounds described herein which are currently in widespread pharmaceutical use are listed in sources well-known to those of skill in the art such as The Merck Index. The constituent used to make a salt of an active drug discussed herein is not critical, provided that it is non-toxic and does not substantially interfere with the desired activity.

A pharmaceutical analog refers to a molecule that resembles a referent compound but which has been modified to replace one or more moieties of the referent molecule with alternate moieties or other substituents that do not ionize and dissociate readily, as occurs in salts. For example, if a hydrogen or chloride moiety is replaced by a methyl group, the resulting molecule would be regarded as an analog. To be covered herein, the analog-producing substituent must not destroy the anti-tussive or anti-dermatitis or other activities of the referent molecule.

Administration of the medicaments to be prepared from the compounds described herein can be by any method capable of introducing the compounds into the bloodstream. Administration can be orally, or by parenteral, intravenous, or subcutaneous injection, for example, as well as by topical or inhalant formulations. In particular topical administration as lotions or ointments is contemplated to treat dermatitis. Likewise, inhalable aerosols are contemplated for treating intractable coughing. An injectable, topical, or inhalant formulation contains a mixture of active compounds with pharmaceutically acceptable carriers or diluents. Various other formulations for oral and injectable medicaments have been described in U.S. Pat. No. 5,166,207 to Smith, which is herein incorporated by reference.

EXAMPLES

The initial testing described in Examples 1 to 3 were preformed on patients having amyotrophic lateral sclerosis (ALS, also called Lou Gehrig's disease). At the time it was thought that DM might have an effect in arresting the progression of ALS and other neurological disorders. Although the studies described in Examples 1 to 3 were done on patients suffering from ALS, most of whom are adults more than 40 years old, no differences were detected in the metabolism of DM in ALS patients, compared to reported findings involving adults who do not have ALS or to one-day tests involving healthy volunteers as a control population.

Example 1

Urinary DM/DR Ratios

Six patients suffering from ALS were administered orally a single 60 mg dextromethorphan dose. Several hours later, a urine sample was collected, and the urine concentrations of dextromethorphan (DM) and dextrorphan (DR) were measured as described below to determine a DM/DR ratio. A low DM/DR ratio indicates that DM is being rapidly oxidized to the DR metabolite in that body of that patient. In a different week, 60 mg of DM and 150 mg of quinidine were orally administered to the same patients, and urinary DM and DR levels and DM/DR ratios were determined again.

DM and DR urinary levels without quinidine were determined by adding 40 mg of thebaine as an internal standard to 1 mL of urine. To this was added 2000 units of betaglucuronidase in 1 mL of acetate buffer (0.1M, pH 5.0). The mixture was incubated for 18 hours at 37° C. and then extracted by adding 1 mL of phosphate buffer (pH 12, 0.10M) and 7 mL of n-butanol/hexane (10:90 v/v). After mixing and centrifugation, the organic layer was transferred to a clean tube, acidified with 400 uL of 0.01N HCL and 20 microliters (uL) of aqueous phase injected into a high performance liquid chromatography (HPLC) system. The HPLC used a phenyl column equilibrated with a mobile phase of acetonitrile:water (51:49 v/v) containing 10 mM $KHPO_4$, 10 mM hexane sulfonic acid, pH 4.0 (flow rate 1.2 mL/min). Detection of thebaine, dextromethorphan and dextrorphan was achieved by fluorescence (Kratos FS-980 Fluorometer) with an excitation wavelength of 228 nm and no emission cutoff filter.

A gas chromatograph/mass spectroscopy (gc/ms) assay was employed for determining dextromethorphan and dextrorphan levels in the presence of quinidine. Briefly, 0.5 ml urine samples were spiked with 500 nanograms (ng) of dimethacrine. The urine pH was adjusted to 0.5 with 0.1M acetate buffer (usually about 1.0 ml), and beta-glucuronidase was added (2000 units/ml urine). The mixture was incubated and shaken at 37° C. for 18 hours. The urine was subsequently adjusted to pH 10–11 with 1.0 mL of phosphate buffer and the urine extracted with 5 mL of dichloromethane. The dichloromethane extract was evaporated under nitrogen, reconstituted in 300 uL of BSTFA and injected onto a gc/ms analyzer equipped with a capillary SE-30 column. Gas chromatographic conditions were: injector and transfer line temperature 250° C., oven 70° C. to 260° C. at 20° C. per minute, and source temperature 180° C. Detection was by selected ion monitoring at m/z 271 for dextromethorphan, 294 for the internal standard, and 329 for dextrorphan. Typical standard curves for dextromethorphan and dextrorphan were provided. Assay sensitivity was 100 ng/ml for dextromethorphan and 400 ng/ml for dextrorphan.

The results, in Table 1, indicate that quinidine is a potent inhibitor of dextromethorphan metabolism. The DM/DR ratio in all test subjects was increased by at least 2 and usually more than 3 orders of magnitude.

TABLE 1

URINGARY DM/DR RATIOS

| Patient # # | DM/DR Ratio, no quinidine | DM/DR Ratio, 150 mg quinidine |
|---|---|---|
| 1 | 0.0048 | 4.090 |
| 2 | 0.0220 | 3.460 |
| 3 | 0.0002 | 0.635 |
| 4 | 0.0003 | 0.420 |
| 5 | | 0.631 |
| 6 | 0.054 | 3.29 |

Follow up tests were done on more than 50 people, including ALS patients and healthy controls who volunteered for one-day tests. The ALS patients received DM and quinidine on a daily basis over several weeks, while control subjects received only a single dose of each drug. The results were very similar to the data contained in Table 1.

Example 2

Plasma Concentrations of DM

Five patients were orally administered 120 mg of DM, with no co-administration of quinidine. Between 10 and 12 hours later, blood was sampled, blood plasma was isolated by centrifugation, and the plasma was analyzed to determine the DM concentration using the thebaine/HPLC method.

During a different week, the same patients were orally administered 60 mg of DM (half the control dosage) and 150 mg of quinidine. Between 10 and 12 hours later, blood was sampled and the plasma was analyzed for DM using thebaine/HPLC.

The results, in Table 2, indicate that quinidine causes a major increase in the concentration of DM in the blood plasma.

TABLE 2

Effects of 150 mg/day quinidine on plasma dextromethorphan levels

| PATIENT | DEXTRO-METHORPHAN DOSE | DEXTRO-METHORPHAN PLASMA LEVEL | QUINIDINE DOSE (MG/DAY) |
|---|---|---|---|
| 1 | 120 MG/DAY | NOT DETECTABLE | 0 |
| | 60 MG ONCE | 33 NG/ML | 150 |
| 2 | 120 MG/DAY | 9.3 NG/ML | 0 |
| | 60 MG ONCE | 29.7 NG/ML | 150 |
| 3 | 120 MG/DAY | NOT DETECTABLE | 0 |
| | 60 MG ONCE | 29.0 NG/ML | 150 |
| 4 | 120 MG/DAY | 16.5 NG/ML | 0 |
| | 60 MG ONCE | 28.8 NG/ML | 150 |
| 5 | 120 MG/DAY | 6.05 NG/ML | 0 |
| | 60 MG ONCE | 45.6 NG/ML | 150 |

Subsequently, plasma levels were determined for about 15 other ALS patients who received dextromethorphan and quinidine over a prolonged period of time. The results were very similar to the data in Table 2.

Example 3

Dose-Response Study

Additional studies were undertaken using a range of dosages of DM to establish a dose-response curve that correlates with plasma concentrations 10 to 12 hours later (determined as described in Example 2). All patients received 150 mg of quinidine daily. The results of those studies are shown in graphical form in FIG. 1, with mean values shown as open squares and standard deviation ranges shown by vertical bars. The ascending line through the median values is a linear approximation; a curve based on more extensive data would probably show a horizontal asymptote.

The results of the tests described in the foregoing Examples indicate that if quinidine is co-administered with DM, then DM circulation in the blood is increased and prolonged, without causing severe side effects. Accordingly, the co-administration of an antioxidant compound such as quinidine in conjunction with DM can increase the effectiveness of DM in any context that depends upon the concentration of DM circulating in the blood.

Example 4

Use of Other Antioxidants

Since some patients cannot tolerate quinidine well, the ability of several other candidate antioxidants to inhibit DM oxidation in various people were tested. In these tests, DM was administered at a constant dosage to various individuals, all were healthy volunteers. DM was taken both before and after a candidate antioxidant was taken, and urine samples were collected at appropriate times and analyzed to determine the quantity of DM and its principle metabolite dextrorphan (DRP) in the urine. A DM/DRP ratio of zero indicated that substantially all of the DM had metabolized into DRP in that patient. A ratio higher than zero indicated that the DM had not been completely metabolized, and a significant quantity of DM remained in the urine.

Twelve healthy volunteers were studied. A first urine sample was taken after initial DM administration, before any antioxidant was administered, to determine a baseline value for that person, and all volunteers were confirmed to be "extensive metabolizers" with baseline DM/DRP ratios or 0.06 or less, except for one "poor metabolizer" with a DM/DRP ratio of 1.338, used to provide a control. Urine samples were analyzed using high performance liquid chromatography (HPLC) to quantitatively evaluate the areas contained within the chromatography peaks displayed by DM and its principle oxidized metabolite (dextrorphan, DRP). A DM/DRP ratio higher than zero indicated that the DM was not completely metabolized and that a significant quantity of DM is present in the urine of the patient; a ratio of 0 indicates that substantially all of the DM was metabolized into DRP.

After the baseline DM/DRP value for each volunteer had been determined, a candidate antioxidant was administered. These agents included quinine sulfate, disulfiram, cimetidine, fluoxetine, propranolol, and nortriptyline. After an appropriate delay, a second urine sample was obtained and analyzed. Each agent was administered to two patients.

The most potent results observed in these tests were from quinamm (quinine sulfate). In one subject, the DM/DRP ration increased from 0.02 (pre-quinine baseline) to 0.09; in the other subject, the DM/DRP ration increased from 0.00 to 0.05. When the other candidate agents were tested, the results indicated high levels of variability between different individuals. For example, in the two subjects who took fluoxetine, the DM/DRP ratio for one increased from 0.00 (pre-drug baseline) to 0.11, while in the other, the ratio decreased from 0.03 to 0.00. In the two subjects who took propranolol, the DM/DRP ratio increased from 0.00 to 0.02 in one, while in the other it decreased from 0.02 to 0.00. In the two subjects who took disulfiram, the DM/DRP ratio increased from 0.06 to 0.08 in one, while it decreased from 0.06 to 0.00 in other. These levels of variability were not surprising, since it is well known that different people have important variations in their oxidative enzymes.

Example 5

Tests On Patients With Intractable Coughing

Three patients were tested under a doctor's supervision, all of whom had been suffering from intractable coughing that had persisted for months. One patient was previously treated with prednisone, an anti-inflammatory steroid, which has adverse long-term side effects. A second patient had coughed for 8 months following a respiratory infection, and would only respond temporarily to cough syrup containing codeine, which is addictive and cannot be taken for long periods. A third patient had such severe coughing following a respiratory infection that he suffered several broken several ribs. Antibiotics for a respiratory infection and anti-inflammatory inhalant drugs were prescribed for a suspected asthmatic condition.

The initial tests on three patients with intractable coughing indicated highly effective results, with virtually no side effects.

Patient EAR, a 70 year old female, had suffered from a recurrent persistent non-productive cough for several years. This cough would respond to prednisone administration, but it would return shortly after the prednisone was discontinued, and continuous medication with prednisone was deemed to be unacceptable. She had tried various cough syrups, with little benefit, and her cough had not responded well to albuteral (a beta-adrenergic bronchodilator) or ipratropium bromide (an anticholinergic bronchodilator); both were administered using a nebulizer-type inhaler. When she was given 1 capsule per day of 75 mg quinidine and 60 mg DM, the cough initially stopped but returned after several days. When the dosage was increased to 2 capsules/day, the cough stopped and did not return. She reported no side effects.

Patient SP, a 38 year old male nonsmoker with no history of asthma, had suffered for about 8 months from a persistent non-productive cough. It receded temporarily when he was given penicillin and a cough syrup with codeine, but it returned after he stopped taking codeine. When he began taking 1 capsule per day of 75 mg quinidine and 60 mg DM, and after a few days, the cough stopped almost completely, and he coughed only rarely during the day. He reported no side effects.

Patient RC, a 43 year old male nonsmoker with no history of asthma, suffered for about 5 months from a cough, which initially began with an upper respiratory viral infection followed by a bacterial infection. The coughing became so severe that it led to fractured ribs. When he first sought medical attention, the cough produced yellow phlegm. The phlegm was cleared up by antibiotics but the cough persisted despite inhalation treatment for a suspected asthma condition with flunisolide (an anti-inflammatory steroid) and inhalation treatment with albuterol. The cough did not substantially improve when the patient took only 1 capsule/day, but when he began taking 2 capsules/day, it improved by roughly 90% within a few days. Although he occasionally coughed, his condition improved so much that he sometimes forgot to take his medication. He reported no side effects.

In all cases, the patients were delighted with the results. The combined DM-antioxidant treatment was very effective in almost completely eliminating coughing that could not be treated adequately by any other medications, and the DM-antioxidant treatment caused minimum reported side effects. The results clearly confirm the effectiveness and utility of the invention.

Example 6

Treatment of Dermatitis

During an initial examination, it was discovered that patient BT, a Caucasian female in her 60's who was suffering from ALS, suffered from a severe dermatologic condition involving lesions which appear in small patches. Her condition had been diagnosed as atopic dermatitis. The etiology is unknown. The patient reported that the lesions were severely itchy, and she had been suffering from it for roughly ten years. She had been prescribed a number of drugs (including various steroids such as prednisone) in an effort to control the itching; the most recent prescription was "Doxepin," a tricyclic antidepressant. None of those agents offered much relief.

The patient began an initial treatment of quinidine alone (150 mg/day) for a week. After it had been established that she did not have an adverse reaction, she began to receive DM as well, beginning at 30 mg/day, and increasing after 1 month to 120 mg/day.

During the second monthly visit after beginning the DM/quinidine treatment, it was found that the patient had obtained an almost total cessation of any itching sensations, with partial resolution of her lesions. A follow-up exam some weeks later indicated that the patient's skin lesions had completely healed with no apparent evidence of scar tissue.

After seeing this result, additional tests were performed by a dermatologic specialist at a nearby university. The first test by the specialist involved a male Caucasian who suffered from severe but intermittent dermatitis. The relapse resolved in less than two weeks after starting treatment. Due to the intermittent nature of the patient's dermatitis, this result could not be conclusively attributed to the DM-antioxidant combination; nevertheless, the disappearance of the relapse promptly after DM-antioxidant treatment began strongly suggested that the DM-antioxidant combination probably had a substantial beneficial effect.

After the initial successes described above, additional studies to determine the effectiveness of DM/quinidine for treating dermatitis were carried out as follows. Patients suffering from dermatitis were first evaluated as to general physical condition, and also evaluated by the physician using a "standardized disease activity scoring" or "lesion score" for the severity of the dermatitis condition. The standardized disease activity score or lesion score is completed by the examining physician who scores on a severity scale of 1 to 5 for both erythema and surface damage for a given area (1 to 5 in size) on the patient's body. The total score was then calculated. The patient indicated on a subjective visual scale the severity of itching and rash due to dermatitis. DM/quinidine were taken in capsule form of 30 mg DM and 75 mg quinidine per capsule. The patient was usually re-examined in two weeks, and then again six weeks or more after the initial exam and receiving the DM/quinidine capsules.

Patient #1 was a 40 year old female patient who suffered from atopic eczema since birth, which flares up with stress. The patient was initially evaluated using the standardized disease activity scoring system and filling out the subjective itching/rash analysis forms. The initial score was 42. The patient indicated the initial itching score as severe, and rash as severe to moderate.

The patient reported side effects of nausea and headache as side effects, and stopped the drugs after five days. She was then placed on a reduced dosage of 30 mg/25 mg DM/quinidine per day. Subsequently, the patent reported the rash and itching almost totally cleared within five days. The two week evaluation showed the patients' total standardized disease activity score was reduced dramatically to 13. The patient's face in particular was strikingly improved. At two weeks, the patient reported the itching reduced to moderate to slight and the rash reduced to moderate to slight. Four weeks later, the patient reported continued headache side effects even when on a reduced dosage. However, the total standardized disease activity score remained lower than initially with a total score of 24. She reported itching in the severe to moderate range, and rash in the moderate range.

Patient #2 was a fifty five year old male with a 20 year history of chronic eczema. The rash was located mainly on the thighs. The initial total standardized disease activity score was initially 12. The patient received a 30 mg/75 mg dosage of DM/quinidine once a day for 5 days, then every 12 hours for the duration. The patient initially reported severe itching and moderate rash. After about 1 month the lesion score remained at 12, but the patient reported itching was reduced to the low moderate range and the rash was reduced to the moderate to slight range. The medications were eventually discontinued due to side effects.

Patient #3 was a fifty four year old male who began suffering from eczema seven or eight years ago. The initial physical exam showed fairly generalized excoriated eczematory dermatitis, which was especially severe on his lower legs. The rash was prone to a secondary infection. The initial lesion score was 112. The patient initially rated his itching as moderate and rash as low moderate. The patient received a 30 mg DM/75 mg quinidine capsule once a day for five days, then every 12 hours for the duration.

After two and a half months, the patient was again evaluated, and received a lesion score of 90. The overall appearance was reported to be improved, and the rash less red. However, the patient reported the same degree of itching and rashes. The patient reported some side effects, most of which disappeared after a few days. However, the patient reported a delay in reaching orgasm, a side-effect which persisted as long as the medications were continued.

Due to the reports of side effects in some patients, the application of DM/quinidine as a topical cream is considered for the treatment of dermatitis.

Example 7

Treatment of Pain

The following pain studies were undertaken to determine if the dextromethorphan/quinidine composition moderates or arrests chronic pain. The effect of the treatment was determined by a patient questionnaire and clinical assessment of the patients by a study physician.

The patient questionnaire asks the patient to assess his or her current level of pain using a linear visual analog scale of 10 where the pain is rated from 10, "pain as bad as it could be" to 0, "no pain". After taking the medications for several weeks, the patients are asked to indicate the current level of pain, as well as to indicate the degree of pain abatement using a linear visual analog pain relief scale of 10 rated from 10, no pain relief to complete 0, pain relief.

The DM dosage administered to the subjects of the study were a total daily dose up to 120 mg of DM, varying with the individual, taken in a capsule formulation in combination with quinidine. Quinidine was administered twice daily with DM up to a total daily dosage 150 mg, varying with the individual subject.

Patient #1 was a 73-year-old female, with a history of diabetes diagnosed ten years earlier. She reported burning and tingling of her feet for two years, which had been increasingly bothersome in the past year. The patient noticed the sensations particularly when she was walking or standing and also at night. The patient did not notice any similar sensations in her hands and denied any significant neck or back pain. The neurological exam was normal, except for the sensory portion of the exam which showed decreased appreciation of pinprick, light touch, and vibratory sense in her distal lower extremities. The neurophysiological assessment confirmed a diagnosis of sensorimotor polyneuropathy.

Prior to going on medication, the patient filled out a visual analog scale, describing her level of pain both on April 11 and shortly before beginning medication on April 25. The patient initially assessed her pain as 3–4 on the pain scale, with 10 indicating pain as bad as it could be. The patient started her medication shortly thereafter, taking 30 mg of dextromethorphan and 75 mg of quinidine once a day.

The follow up exam was give approximately a month later on May 9. The patient reported to be feeling better with much less pain. She noted the tingling in her feet and pain in her right leg was alleviated. Her sleep patterns were the same. She reported there were no side effects taking DM/quinidine at a dosage of 30 mg/75 mg twice a day. At that point her dosages were increased to 60 mg of dextromethorphan and 75 mg of quinidine twice a day.

Two weeks later on May 19, the patient filled out a visual analog pain relief scale, indicating that the level of pain was substantially improved, now rated as 1 to 2 with 10 rated as pain as bad as it could be, indicating that she had obtained significant pain relief. The overall impression was that her pain was much better. She reported feeling well with no side effects. The tingling had diminished compared to the past when it occurred 3 to 4 times per week. On May 23 the patient reported her level of pain as between 0 and 1, which 0 indicating not pain. The patient then stopped taking the DM/quinidine and reported back on May 27 that she was well without any significant return of pain. On May 31, 1994 she reported that the tingling in feet and hands had returned and she was not sleeping as well. The patient then requested to be placed back on the medication.

Patient #2 was a 53-year-old male with painful sensations on his right side. This patient had suffered from a stroke in 1991. A CT scan at the time showed a left posterior cerebral infarct. The patient also had coronary artery disease and bypass surgery in 1991, and suffered from diabetes and hypertension. Neurological findings included visual and sensory loss, and right-sided weakness. Over the past 4 to 5 months, the patient had noted a buzzing sensation on his right side and an icy or heat sensation, which affected the right side of his face, arm, chest and leg. His left side was unaffected. This unpleasant sensation was particularly bothersome at night occurring for up to five minutes at a time, and off and on all day long. The buzzing sensation was generally always present. The sensation was uncomfortable, not very painful at times, but caused the patient a great deal of anxiety. In addition, the patient has noted some tingling in the bottom of both feet from time to time, a high pitched hum in his ears and lightheadedness when his head was tipped back. In addition, this patient had reported tinnitus.

The patient was assessed by the examining physician as having classic symptoms of Dejerine-Roussy Syndrome, which is pain emanating from a diseased thalamus secondary to stroke.

The patient initially assessed his pain on the visual analog scale as varying between 9 and 10 at peak period to between 5 and 6 at other times, with 10 indicating pain as bad as it could be. Six weeks after being placed on the medication at a dosage of 30 mg DM/75 mg quinidine twice a day, the patient indicated pain at between 7 and 8 at peak times, with pain between 3 and 4 at other times using the visual analog scale. At this time, the patient indicated the level of pain relief as between 2 and 3, with 0 indicating complete pain relief, and 10 indicating no pain relief. One week after stopping the medications, the patient indicated a return to a pain level at between 7 and 8.

Patient #3 was a 63 year old male who had been diagnosed with diabetes for 25 years. He also suffered from arthritis and hypertension. The patient complained of numbness in his hands for two years. In addition, the patient noted that his feet hurt for the past three years. Throbbing pain interfered with sleep and required pain pills. He also had pain at the tip of his buttocks and intermittent neck pain. The neurological examination was remarkable for markedly decreased pinprick sensation in the patient's feed and distal fingers, with normal position sense and slightly decreased vibration sense. The clinical assessment was that the patient had primarily a sensory neuropathy secondary to his diabetes.

Prior to starting the DM-quinidine treatment at a dosage of 30 mg dextromethorphan and 75 mg quinidine at twelve hour intervals, the patient completed two visual analog scales describing his level of pain, one on April 11 and one shortly before beginning his medication on May 9. The patient initially rated his pain at between 5 and 6, and one month later as between 6 and 7, with 10 indicating the pain was as bad as it could be. The patient began taking DM-quinidine in the dosage of one tablet of 30 mg of dextromethorphan and 75 of quinidine twice a day.

On May 16 the patient noted via a telephone conversation that he felt lightheaded and his stomach was mildly upset, but he otherwise felt okay and he was continuing on the medication. The patient followed up in the office on May 23 and at that point, described that his pain was reduced from occurring nightly to only occurring occasionally, and was reduced overall to about 70–80% of what was previously experienced. He was not taking any other types of pain pills and had awakened only once at night from pain since being on the medication. He reported still having some intermittent light pain. Side effects were reported to be a little nausea, but not every day. At this time he rated his pain relief as between 1 and 2, with 0 indicating complete pain relief, and his current level of pain at between 1 and 2, with zero indicating no pain. The examining physician rated the patient's level of pain as much better.

On May 31 the patient reported pain in each foot during the previous week. He continued to take one tab of 30/75 DM/Quinidine. After two more weeks, he stopped taking the medication. On July 19, the patient completed another visual analog scale describing his current level of pain. He reported the level of pain as between 2 and 3, which remained lower that his initial assessment, even though he had discontinued his medication.

Example 8

Treatment of Tinnitus

Patient #2 from the pain study described in Example 7 also had suffered from chronic ringing in the ears, known as tinnitus, for a number of years. As a part of the pain study, this patient had taken 30 mg DM/75 mg quinidine capsules twice a day to relieve thalamic pain syndrome resulting from a stroke three years earlier. After about two weeks of taking the DM/quinidine capsules to relieve his pain, this patient reported an unexpected and total cessation of his chronic tinnitus. This evidence, together with published studies that NMDA receptors are found in the cochlear system which is the presumed site of the tinnitus disorder indicate that the DM/antioxidant combination is a promising therapy for tinnitus.

These examples demonstrate that the combination of dextromethorphan and an antioxidant such as quinidine are effective at treating intractable disorders, including intractable coughing, chronic pain, dermatitis, tinnitus and sexual dysfunction. Although this invention has been described with reference to the presently preferred embodiments, it is understood that various modifications can be made without departing from the spirit of the invention. According, the invention is limited only by the following claims.

We claim:

1. A method of increasing the effectiveness of dextromethorphan in treating chronic or intractable pain, comprising administering to a patient suffering from chronic or intractable pain a therapeutically effective dosage of dextromethorphan or a pharmaceutically acceptable salt thereof, in combination with a therapeutically effective dosage of a debrisoquin hydroxylase inhibitor.

2. The method of claim 1 wherein the debrisoquin hydroxylase inhibitor is selected from the group consisting of quinidine, quinine, and pharmaceutically acceptable salts thereof.

3. The method of claim 2 wherein quinidine is administered at a dosage not exceeding about 300 milligrams per day.

4. The method of claim 1 wherein the debrisoquin hydroxylase inhibitor is selected from the group consisting of disulfiram, fluoxetine, propranolol, nortriptyline, and pharmaceutically acceptable salts thereof.

5. A method of using dextromethorphan to treat chronic or intractable pain, comprising administering, to a patient suffering from chronic or intractable pain, dextromethorphan or a pharmaceutically acceptable salt thereof in combination with a debrisoquin hydroxylase inhibitor, wherein the dextromethorphan or salt thereof and the inhibitor are administered at combined dosages which render the dextromethorphan therapeutically effective in substantially reducing chronic or intractable pain, without causing unacceptable side effects.

6. The method of claim 5 wherein the debrisoquin hydroxylase inhibitor is selected from the group consisting of quinidine, quinine, and pharmaceutically acceptable salts thereof.

7. The method of claim 6 wherein quinidine is administered at a dosage not exceeding about 300 milligrams per day.

8. The method of claim 5 wherein the debrisoquin hydroxylase inhibitor is selected from the group consisting of disulfiram, fluoxetine, propranolol, nortriptyline, and pharmaceutically acceptable salts thereof.

9. A method of using dextromethorphan in treating tinnitus, comprising administering, to a patient suffering from tinnitus, dextromethorphan or a pharmaceutically acceptable salt thereof in combination with a debrisoquin hydroxylase inhibitor, wherein the dextromethorphan or salt thereof and the debrisoquin hydroxylase inhibitor are administered at combined dosages which render the dextromethorphan thereof therapeutically effective in substantially reducing tinnitus without causing unacceptable side effects.

10. The method of claim 9 wherein the debrisoquin hydroxylase inhibitor is selected from the group consisting of quinidine, quinine, and pharmaceutically acceptable salts thereof.

11. The method of claim 10 wherein quinidine is administered at a dosage not exceeding about 300 milligrams per day.

12. The method of claim 9 wherein the debrisoquin hydroxylase inhibitor is selected from the group consisting of disulfiram, fluoxetine, propranolol, nortriptyline, and pharmaceutically acceptable salts thereof.

13. A method for treating sexual dysfunction, comprising administering to a patient in need thereof dextromethorphan or a pharmaceutically acceptable salt thereof in combination with a debrisoquin hydroxylase inhibitor, at combined dosages which render the dextromethorphan thereof therapeutically effective in treating the sexual dysfunction.

14. The method of claim 13 wherein the patient is a male who suffers from priapism or premature ejaculation.

15. The method of claim 13 wherein the debrisoquin hydroxylase inhibitor is selected from the group consisting of quinidine, quinine, and pharmaceutically acceptable salts thereof.

16. The method of claim 15 wherein quinidine is administered at a dosage not exceeding about 300 milligrams per day.

17. The method of claim 13 wherein the debrisoquin hydroxylase inhibitor is selected from the group consisting of disulfiram, fluoxetine, propranolol, nortriptyline, and pharmaceutically acceptable salts thereof.

18. A unit dosage formulation for treatment of chronic or intractable pain, comprising:

(a) dextromethorphan or a pharmaceutically acceptable salt thereof, and, (b) a debrisoquin hydroxylase inhibitor, in a combined form that is designed for oral ingestion by humans, wherein the dextromethorphan or salt thereof and the debrisoquin hydroxylase inhibitor are present at a combined dosage which renders the dextromethorphan therapeutically effective in substantially reducing chronic or intractable pain, without causing unacceptable side effects.

19. The unit dosage formation of claim 18, comprising a digestible capsule which encloses the dextromethorphan or pharmaceutically acceptable salt thereof and the debrisoquin hydroxylase inhibitor.

20. The unit dosage formulation of claim 18, wherein the debrisoquin hydroxylase inhibitor is selected from the group consisting of quinidine, quinine, and pharmaceutically acceptable salts thereof.

21. The unit dosage formulation of claim 20, wherein the dosage of quinidine is 300 milligrams/day or less.

22. The unit dosage formulation of claim 18, wherein the debrisoquin hydroxylase inhibitor is selected from the group consisting of disulfiram, fluoxetine, propranolol, nortriptyline, and pharmaceutically acceptable salts thereof.

* * * * *